United States Patent
Overstreet

(10) Patent No.: US 10,549,089 B2
(45) Date of Patent: Feb. 4, 2020

(54) METHOD AND SYSTEM FOR RAPID ACQUISITION OF EVOKED COMPOUND ACTION POTENTIAL RECORDINGS

(71) Applicant: Oticon Medical A/S, Smørum (DK)

(72) Inventor: Edward Overstreet, Vallauris (FR)

(73) Assignee: OTICON MEDICAL A/S, Smørum (DK)

( * ) Notice: Subject to any disclaimer, the term of this patent is extended or adjusted under 35 U.S.C. 154(b) by 568 days.

(21) Appl. No.: 15/381,417

(22) Filed: Dec. 16, 2016

(65) Prior Publication Data

US 2017/0173332 A1   Jun. 22, 2017

(30) Foreign Application Priority Data

Dec. 17, 2015   (EP) ..................................... 15200749

(51) Int. Cl.
   *A61N 1/00* (2006.01)
   *A61N 1/05* (2006.01)
(52) U.S. Cl.
   CPC ................................. *A61N 1/0541* (2013.01)
(58) Field of Classification Search
   None
   See application file for complete search history.

(56) References Cited

U.S. PATENT DOCUMENTS

| 6,915,166 B1 | 7/2005 | Stecker et al. |
| 2009/0259277 A1 | 10/2009 | Cornejo Cruz et al. |
| 2015/0112408 A1 | 4/2015 | Kals |

*Primary Examiner* — Mallika D Fairchild
(74) *Attorney, Agent, or Firm* — Birch, Stewart, Kolasch & Birch, LLP

(57) ABSTRACT

According to an embodiment, a system for acquiring ECAP recordings at a later session for a cochlear implant patient is disclosed. The system includes a receiving unit configured to receive, corresponding to an electrode, a stored prior individual value from a plurality of stored prior individual values of ECAP/an ECAP prior growth function, the plurality of stored prior individual values or the ECAP prior growth function being obtained at a previous session. Furthermore, a processing unit configured to process the received prior individual value/ECAP growth function to determine a stimulus signal value corresponding to the received individual value/a selected point on the ECAP prior growth function, instruct a signal delivery unit to provide to the electrode a first stimulus signal comprising a first level that is same or above said stimulus signal value, and determine a resulting ECAP generated in response to said first stimulus signal.

20 Claims, 6 Drawing Sheets

METHOD AND SYSTEM FOR RAPID ACQUISITION OF EVOKED COMPOUND ACTION POTENTIAL RECORDINGS

FIELD

The present disclosure generally relates to methods and systems for obtaining Evoked Compound Action Potential (ECAP) recordings. In particular, the disclosure relates to such a method and system for rapid acquisition of ECAP recordings in patients where prior ECAP growth function as have already been obtained. The disclosed method and system may be used in connection with cochlear implants (Cis) in hearing impaired persons.

BACKGROUND

Generally, there is a need to obtain data from the implanted components of a cochlear implant. Such data collection enables detection and confirmation of the normal operation of the device, and allows stimulation parameters to be optimized to suit the needs of individual recipients. This includes data relating to the response of the auditory nerve to stimulation.

Typically, following the surgical implantation of a cochlear implant, the implant is fitted or customized to conform to the specific recipient demands. This involves the collection and determination of patient-specific parameters such as threshold levels (T levels) and maximum comfort levels (C levels) for each stimulation channel. The procedure is performed manually by applying stimulation pulses for each channel and receiving an indication from the implant recipient as to the level and comfort of the resulting stimulation.

One method of interrogating the performance of an implanted cochlear implant and making objective measurements of patient-specific data such as T and C levels is to directly measure the response of the auditory nerve to an electrical stimulus. The direct measurement of neural responses, commonly referred to as Electrically Evoked Compound Action Potentials (ECAPs) in the context of cochlear implants, provides an objective measurement of the response of the nerves to electrical stimulus. Following electrical stimulation, the neural response is caused by the superposition of single neural responses at the outside of the axon membranes. The measured neural response is transmitted to a system located external to the CI recipient, typically via a telemetry system. This provides measurements of the ECAPs from within the cochlea in response to various stimulations. Generally, the neural response resulting from a stimulus presented at one electrode is measured at a neighboring electrode, although this need not be the case.

A prior art method for obtaining ECAP's is illustrated with reference to FIG. 1 and FIG. 2.

In FIG. 1 there is shown an ECAP(t) plot 1 of a sequence of measurements containing seven ECAP measurements 2 through 8 which show a clearly distinguishable neural response. Thus, each measurement waveform 2 through 8 comprises a clearly distinctive negative peak (N1) 10 and a clearly distinctive positive peak (P1) 9. Only one positive and negative peak is shown in FIG. 1 for clarity. The parameter in the plot of FIG. 1 is the neural stimulus, for instance stimulus current level (see FIG. 2). The strongest neural stimulus is used to obtain the response 2 and the weakest neural stimulus is used to obtain the response 8.

The measurement waveforms toward the top of the graph depicted in FIG. 1 (measurement waveforms 2 and 3, for example) indicate a stronger neural response to a relatively large neural stimulus, while the measurement waveforms toward the bottom of the graph (measurement waveforms 7 and 8, for example) indicate a weaker neural response with reduced neural stimuli strengths. As it clearly appears from FIG. 1, a progressively more distinct neural response, i.e. a neural response showing distinct peaks (such as 9) and dips (such as 10) is obtained for progressively more powerful neural stimuli. At weak neural stimuli, it becomes progressively more difficult to determine if a neural response is in fact elicited.

Distinguishing between measurements that display a neural response such as those of FIG. 1 and measurements which do not display a neural response is an important aspect of performing such measurements. This task can be extremely difficult, for instance when the combination of stimulus artefact and noise gives the appearance of a weak neural response.

In particular, the minimum stimulus current level required to evoke a neural response at a given electrode in a cochlear implant is referred as the threshold level (for that particular electrode, i.e. for the frequency corresponding to the placement of this electrode in the patients cochlear). In general, the threshold level profiles are correlated with MAP T and C profiles, and thus threshold levels can be used as a guide for MAP fitting. Accordingly, accurate determination of threshold level values for each electrode and for each recipient is highly desirable.

One conventional approach to determine the threshold level values is the Amplitude Growth Function (AGF) method. The AGF method is based on the premise that the peak-to-peak amplitude of a neural response increases linearly with stimulus current level. However, the relationship is more accurately defined by a sigmoidal function. By obtaining the peak-to-peak amplitude value at different stimulus current levels, a regression line may be drawn through these measurement points and extrapolated to the point at which the peak-to-peak amplitude becomes zero, thus indicating the threshold stimulus level.

For example, FIG. 2 illustrates a typical prior art measurement plot 11 of peak-to-peak amplitude ECAPs (in microvolts) vs. stimulus current level (in digitized current level units). The threshold value corresponds to the amplitude 0 V and is indicate by the line 14 in FIG. 2. In FIG. 2, the current level scale shown extends from 96 to 192 current level units with each unit representing an increasingly lager current. The individual measurement results are indicated by the dots, such as 12 in the plot 11. Typically, the measurements can be fitted with a number of regression lines, but in the example shown in FIG. 2 the regression 13, yielding a possible threshold value of 148 current level units is shown. As it appears from FIG. 2, the regression line 13 intercepts the x-axis (the current level axis) at a point 15.

Prior art methods of establishing the neural excitation threshold suffers from a number of disadvantages of which some are listed below:

(1) Typically, the AGF approach requires a significant number of measurements above the threshold to enable a regression line to be determined.

(2) An alternative method of threshold determination is visual detection. The visual-detection method is more subjective, where threshold is determined as the lowest current level for which an ECAP waveform can be visually identified by a human observer. Unlike the linear regression method which requires multiple responses, the visual detection method utilizes a single response. This method works best in systems with a low noise floor. For systems with a high noise floor, ECAP responses occurring at low current levels may be obscured, resulting in artificially elevated threshold estimates. Visual detection depends critically on the acuity of the observer to distinguish between neural responses and artefact or noise. Visual detection of threshold is also observer-dependent.

(3) ECAP diagnostics often require significant clinical time. Existing data collection methods do not leverage pre-existing patient data during follow-up appointments and/or rechecking objective measures.

It is consequently desirable to provide a method and system that significantly reduces the number of suprathreshold level measurements required at a later recording session for obtaining the Evoked Compound Action Potential Recordings in patients provided with a cochlear implant.

It is further desirable to provide a method of as stated above that can be carried out significantly faster than known prior art methods.

SUMMARY

According to the present disclosure, the advantages are obtained by a method and system that determines growth function stability with sparsely sampled stimulation levels at a later session across prerecorded channels from a prior session and uses previously stored waveform data from prior recordings in the same configuration on the same patient to assist in determining the statistical validity of the response in the later session. The sparsely sampled stimulation levels may refer to utilizing a subset of ECAP measurements from the prior session.

Thus, according to the present disclosure, instead of searching for threshold responses (as done in the prior art methods) which requires the greatest amount of time, prior growth function data or neural responses are used. Neural stimulation at a known supra threshold value is applied to check if the neural response is of the same magnitude or within a predetermined variation range at the later session as before determined by prior neural recordings at the prior session in the same configuration. Following the method according to the present disclosure, it would no longer be necessary to recollect all of the growth functions to ascertain whether or not there had been a significant change in the patient's neural response patterns.

The prior session and the later session refer to ECAP recording session where the later session is subsequent to the prior session, for example after 1 month, 2 months, 3 months and so on.

According to an embodiment, a system for acquiring evoked compound action potential (ECAP) recordings at a later session for a patient provided with a cochlear implant comprising an implanted array of electrodes is disclosed. The system includes a receiving unit and a processing unit. The receiving unit is configured to receive, corresponding to an electrode of the implanted array of electrodes, a stored prior individual value from a plurality of stored prior individual values of evoked compound action potentials (ECAP) or an ECAP prior growth function corresponding to the stored plurality of prior individual values of the ECAP, the plurality of stored prior individual values or the ECAP prior growth function being obtained at a previous session. The processing unit is configured to process the received prior individual value or ECAP growth function to determine a stimulus signal value corresponding to the received individual value or a selected point on the ECAP prior growth function, instruct a signal delivery unit to provide to the electrode a first stimulus signal comprising a first level that is same or above said stimulus signal value, and determine a resulting evoked compound action potential generated in response to said first stimulus signal.

The stored prior individual values or the ECAP prior growth function may be retrieved from a locally available or a remote database. The values or the growth function are channel specific, i.e. specific to an electrode of the array of electrodes that is place-frequency matched in its positioning within cochlear of the patient. For example, in an electrode array including 20 electrodes, each electrode has a different frequency distribution as defined by the associated audio frequency range. As an illustrative example only, electrode number 1 may have an associated frequency range of around 6500-8000 Hz defining a channel, similarly electrode number 2 may have an associated frequency range of 200-450 Hz defining another channel.

In one embodiment, the system includes a storage unit (locally available or remote database). The storage unit is configured to store a prior individual value/plurality of prior individual values of evoked compound action potentials (ECAP) and/or an ECAP prior growth function corresponding to the stored plurality of prior individual values of the ECAP from the previous sessions. The storage unit is further configured to provide the stored prior individual value/ plurality of stored prior individual values of evoked compound action potentials (ECAP) or an ECAP prior growth function corresponding to the stored plurality of prior individual values of the ECAP in response to a request from the processing unit.

The threshold level corresponds to the stimulus level corresponding to patient's minimum hearing threshold. For example, the stimulus signal is an electrical current and the stimulus signal level refers to the current level associated with patient's minimum hearing threshold.

In an embodiment, that the first stimulus signal or another such as second or subsequent stimulus signal comprising a level that is at least same or above stimulus level corresponding to patient's minimum hearing threshold. The above is defined that the level is within a predefined percentage above the stimulus signal level. Such predefined percentage may be at least 1%, or at least 2%, or at least 3% and so on.

In a further embodiment, the processing unit is configured to instruct a comparator, to determine a value difference between a value of the resulting evoked compound action potential and the received stored prior individual value from the prior session. The processing unit is further configured to instruct a notifier, to notify that a threshold level corresponding to the electrode is unchanged if the determined value difference is equal to or below a predetermined value difference and the received stored prior individual value related to the threshold level determined in the previous session.

The notifier may be configured to notify using one or more notification mechanisms. This may include visual notification such as a text message or numerical representation or as a measurement dot on a measurement plot.

In a further embodiment, the system is configured to utilize same ECAP recording parameters during the later session as utilized during the previous session. The recording parameters includes one or more of recording delay, amplifier gain, number of averages, stimulation rate, artifact removal scheme, and recording electrode. The skilled person would appreciate that other parameters may also be included. The recording delay refers to the amount of time between offset of the probe pulse represented by the stimulus signal and onset of recording. Recording electrode may include two recording electrode apical to the stimulating electrode but this need not be the case. Amplifier gain may be important if the amplifier saturation presents a significant problem. This may be resolved by extending the recording delay or recording from an electrode that is farther away. As with any evoked potential, increasing the number of averages typically reduces the amount of noise in the recorded ECAP response. The number of averages could vary for example 16, 32, 64 or even more. The stimulation rate may be manually chosen or automatically set to a default value. The significance of these recording parameters are conventionally known and the skilled person would be able to decide an optimal set of the recording parameters that may be used for both the prior session as well as later session.

The same configuration refers to the prior session and the later session having the same recording parameters.

In yet another embodiment, the system includes the receiving unit and the processing unit. Ther receiving unit is configured to receive, corresponding to the electrode of the implanted array of electrodes, the at least two prior individual values from the plurality of stored prior individual values of evoked compound action potentials (ECAP) or the ECAP prior growth function corresponding to the stored plurality of prior individual values of the ECAP, the plurality of stored prior individual value or the ECAP prior growth function being obtained at a previous session. The processing unit is configured to process the at least two received prior individual values or ECAP growth function to determine at least two stimulus signal values corresponding to the at least two received prior individual values or at least two selected points on the ECAP prior growth function, instruct a signal delivery unit to provide to the electrode a first stimulus signal and a second stimulus signal, the first signal comprising a first level that is same or above one of the at least two stimulus signal values and the second signal comprising a second level that is same or above the other of the at least two stimulus signal threshold values, and determine at least two resulting evoked compound action potentials elicited in response to said first stimulus signal and second stimulus signal.

In an embodiment, the system includes a regression line generator, a slope estimator, a comparator, and processing unit. The regression line generator configured to generate a prior regression line based on the at least two received prior individual values and a later regression line based on the determined at least two resulting evoked compound action potentials. The slope estimator configured to determine a prior slope corresponding to the prior regression line and a later slope corresponding to the later regression line. The comparator configured to compare the prior slope with the later slope and determine a slope difference between the prior slope and later slope. The processing unit configured to instruct a notifier, to notify that a threshold level corresponding to the electrode is unchanged if the determined slope difference is equal to or below a predetermined slope difference value.

In an embodiment, the system includes a regression line generator, a slope estimator, a comparator, and processing unit. The regression line generator configured to generate a later regression line based on the determined at least two resulting evoked compound action potentials. The slope estimator configured to determine a prior slope of the received ECAP prior growth function and a later slope corresponding to the later regression line. The comparator configured to compare the prior slope with the later slope and determine a slope difference between the prior slope and later slope. The processing unit configured to instruct a notifier, to notify that a threshold level corresponding to the electrode is unchanged if the determined slope difference is equal to or below a predetermined slope difference value.

In embodiments where the processing unit configured to instruct a notifier, to notify that a threshold level corresponding to the electrode is unchanged if the determined slope difference is equal to or below a predetermined slope difference value, the processing unit is further configured to determine if a value difference between a value of the prior ECAP and corresponding value from resulting evoked compound action potential is within a predetermined value difference. The corresponding value is defined by stimulus signal level that relates, i.e. same or above, to the value of the prior ECAP. The processing unit is further configured to instruct a notifier, to notify that a threshold level corresponding to the electrode is unchanged if the determined value difference is also equal to or below a predetermined value difference. This allows for avoiding false positive based on predetermined slope difference value because there might be conditions where two values, lying outside the predetermined value difference may give same slope as the slope of the prior growth function.

In the above embodiment, the predetermined value difference for a value closer to the zero line is smaller than the predetermined value difference for a value that is away from the zero line. This allows for ensuring that the criteria for making slope comparison between prior growth function and later regression line is more reliably linked to slopes of the regression lines with smaller variation.

In an embodiment, the ECAP growth function is obtained by regression analysis thereby providing a regression function for ECAP measurements carried out at the at least one electrode such as at each individual of the electrodes at a plurality of different stimulus signal levels during the prior session.

In an embodiment, the regression analysis comprises linear regression. This may further include determining a regression line slope and a point of interaction with a zero line of the ECAP. The regression line slope is defined as a prior slope of a regression line, which is based on the ECAP measurements from the prior session.

In an embodiment, the stimulus threshold value is the stimulus signal level corresponding to the point of interaction (zero crossing) of the grown function/regression line with the zero line of the ECAP.

In an embodiment, the receiver unit is configured to receive a prior threshold level, corresponding to the electrode, from a previous session. Alternatively, the processing unit is configured to determine prior threshold level from zero crossing of the prior regression line/received ECAP growth function with a zero line.

In an embodiment, the processing unit is configured to determine a zero crossing of the later regression line with a zero line, and obtaining a later threshold value represented by the stimulus signal level corresponding to the point of zero crossing. The processing unit is further configured to determine a threshold value difference between the later threshold value and the prior threshold level; and instruct the notifier to notify that a threshold level corresponding to the electrode is unchanged if the determined threshold value difference is equal to or below a predetermined value difference.

In an embodiment, the processing unit is configured to instruct the notifier to alert an operator to manually determine the value of the ECAP for estimating threshold value i) if the determined slope difference is above the predetermined slope difference value; and/or ii) if the determined value difference or determined threshold value difference is above the predetermined value difference.

In an embodiment, the predetermined slope difference and/or predetermined value difference is based on a sample population, wherein the predetermined slope difference and/or predetermined value difference is determined based on successful ECAP measurements performed manually during multiple subsequent sessions for each CI user included in a sample population.

In an embodiment, the predetermined slope difference and/or predetermined value difference is a function of frequency channel. For example, the predetermined slope difference and/or predetermined value difference is for low frequency channels is lower than that for high frequency channels.

In an embodiment, a non-transitory computer readable medium is disclosed. The non-transitory computer readable medium is encoded with instructions, which when executed by a system, causes the system comprising the receiving unit to receive, corresponding to an electrode of the implanted array of electrodes, a stored prior individual value from a plurality of stored prior individual values of evoked compound action potentials (ECAP) or an ECAP prior growth function corresponding to the stored plurality of prior individual values of the ECAP, the plurality of stored prior individual values or the ECAP prior growth function being obtained at a previous session. Further, the non-transitory computer readable medium is encoded with instructions, which when executed by a system, causes the system comprising a processing unit to process the received prior individual value or ECAP growth function to determine a stimulus signal value corresponding to the received individual value or a selected point on the ECAP prior growth function, instruct a signal delivery unit to provide to the electrode a first stimulus signal comprising a first level that is same or above said stimulus signal value, determine a resulting evoked compound action potential generated in response to said first stimulus signal.

In an embodiment, the non-transitory computer readable medium encoded with instructions, which when executed by a system, causes the system comprising a processing unit to instruct a comparator, to determine a value difference between a value of the resulting evoked compound action potential and the received stored prior individual value from the prior session; and instruct a notifier, to notify that a threshold level corresponding to the electrode is unchanged if the determined value difference is equal to or below a predetermined value difference and the received stored prior individual value related to the threshold level determined in the previous session.

In an embodiment, the non-transitory computer readable medium encoded with instructions, which when executed by a system, causes the system comprising a regression line generator to generate a prior regression line based on the at least two received prior individual values and a later regression line based on the determined at least two resulting evoked compound action potentials. Further, the non-transitory computer readable medium, causes the system comprising a slope estimator to determine a prior slope corresponding to the prior regression line and a later slope corresponding to the later regression line. Further, the non-transitory computer readable medium, causes the system comprising a comparator to compare the prior slope with the later slope and determine a slope difference between the prior slope and later slope. Further, the non-transitory computer readable medium, causes the system comprising a the processing unit to instruct a notifier, to notify that a threshold level corresponding to the electrode is unchanged if the determined slope difference is equal to or below a predetermined slope difference value.

In an embodiment, the non-transitory computer readable medium encoded with instructions, which when executed by a system, causes the system comprising a regression line generator to generate a later regression line based on the determined at least two resulting evoked compound action potentials. Further, the non-transitory computer readable medium, causes the system comprising a slope estimator to determine a prior slope of the received ECAP prior growth function and a later slope corresponding to the later regression line. Further, the non-transitory computer readable medium, causes the system comprising a comparator to compare the prior slope with the later slope and determine a slope difference between the prior slope and later slope. Further, the non-transitory computer readable medium, causes the system comprising the processing unit configured to instruct a notifier, to notify that a threshold level corresponding to the electrode is unchanged if the determined slope difference is equal to or below a predetermined slope difference value.

In an embodiment, the non-transitory computer readable medium encoded with instructions, which when executed by a system, causes the system comprising the processing unit to determine a zero crossing of the later regression line with a zero line, and obtaining a later threshold value represented by the stimulus signal level corresponding to the point of zero crossing; determine a threshold value difference between the later threshold value and the prior threshold level; and instruct the notifier to notify that a threshold level corresponding to the electrode is unchanged if the determined threshold value difference is equal to or below a predetermined value difference.

In an embodiment, the non-transitory computer readable medium encoded with instructions, which when executed by a system, causes the system to perform any of the features previously described in relation to the system embodiments.

In an embodiment, a method for acquiring evoked compound action potential (ECAP) recordings at a later session for a patient provided with a cochlear implant comprising an implanted array of electrodes is disclosed. The method includes receiving, corresponding to an electrode of the implanted array of electrodes, a stored prior individual value from a plurality of stored prior individual values of evoked compound action potentials (ECAP) or an ECAP prior growth function corresponding to the stored plurality of prior individual values of the ECAP, the plurality of stored prior individual values or the ECAP prior growth function being obtained at a previous session. The method further includes processing the received prior individual value or ECAP growth function to determine a stimulus signal value corresponding to the received individual value or a selected point on the ECAP prior growth function, instructing a current delivery unit to provide to the electrode a first stimulus current signal comprising a first level that is same or above said stimulus signal value; and determining a resulting evoked compound action potential elicited in response to said first stimulus signal.

In an embodiment, the method further includes determining a value difference between a value of the resulting evoked compound action potential and the received stored prior individual value from the prior session; and notifying that a threshold level corresponding to the electrode is unchanged if the determined value difference is equal to or below a predetermined value difference and the received stored prior individual value related to the threshold level determined in the previous session.

In yet another embodiment, the method includes generating a later regression line based on the determined at least two resulting evoked compound action potentials with or without generating a prior regression line based on the at least two received prior individual values, determining a prior slope corresponding to the prior regression line/ECAP prior growth function and a later slope corresponding to the later regression line, comparing the prior slope with the later slope and determining a slope difference between the prior slope and later slope; and notifying a threshold level corresponding to the electrode is unchanged if the determined slope difference is equal to or below a predetermined slope difference value.

In another embodiment, the method includes determining a zero crossing of the later regression line with a zero line, and obtaining a later threshold value represented by the stimulus signal level corresponding to the point of zero crossing; determining a threshold value difference between the later threshold value and the prior threshold level; and notifying that a threshold level corresponding to the electrode is unchanged if the determined threshold value difference is equal to or below a predetermined value difference.

In an embodiment, the method includes any of the features previously described in relation to the system embodiments.

According to an embodiment, the predetermined value difference and/or predetermined slope difference value may include an acceptable range of variation between the response measurement made at the later session and the response measurement received from the prior session.

In an embodiment, the later slope of the ECAP later growth function is based on at least two stimulus signals. The at least two stimulus signals being such that
i) the levels of the at least two stimulus signals are above said threshold value, corresponding to threshold level from the previous session, or ii) the level of one of the at least stimulus signals is same as said stimulus signal threshold value and the level of another of the at least stimulus signals is above said stimulus signal threshold value wherein said threshold value corresponding to threshold level from the previous session; and
the levels of the at least two stimulus signals are different from each other; with our without
the levels of the at least two stimulus signals are chosen from signal levels of stimulus signals associated with said stored prior individual values of evoked compound action potentials (ECAP). Thus, one may envisage the levels of the at least two stimulus signals as a subset of the signal levels of stimulus signals associated with stored prior individual values of ECAP.

In another embodiment, determining the later growth function and comparing the slope difference during the later session includes
carrying out a second evoked compound action potential measurement at the same at least one electrode using a second stimulus signal level and the same recording parameters, the second stimulus signal level being above said stimulus signal threshold value, the second stimulus signal level being above said stimulus signal threshold level and different from the first stimulus signal level;
determining the later slope of an ECAP later growth function based on the evoked compound action potential obtained by applying said first stimulus signal level and second stimulus signal level to said at least one electrode; and
determining the slope difference between later slope of the ECAP later growth function and prior slope of the ECAP prior growth function determined from said prior stored individual values of evoked compound action potentials (ECAP) or corresponding ECAP Growth function.

In the embodiment disclosed in the preceding paragraph, the skilled person would appreciate that utilizing the first stimulus signal level and the second stimulus signal level allows for obtaining ECAP measurements, which in turn allow for determining the later slope without the need of obtaining a large number of measurements during the later session.

In an embodiment, the method further includes determining the later slope of the ECAP later growth function based on the evoked compound potential obtained by applying the first stimulus signal level, second stimulus signal level and one or more subsequent stimulus signal levels to said at least one electrode; and determining the slope difference between the later slope and the prior slope. The one or more subsequent stimulus signals are above said stimulus signal threshold level and different from the first stimulus signal level, second stimulus signal level and from one another.

In an embodiment, the first signal level and the second signal level are chosen from signal levels of stimulus signals associated with said stored prior individual values of evoked compound action potentials (ECAP). Additionally or alternatively, the one or more subsequent signal level are chosen from signal levels of stimulus signals associated with said stored prior individual values of evoked compound action potentials (ECAP).

In an embodiment, a zero crossover (crossing) of the ECAP later growth function with the zero line is determined, and a later threshold value represented by the stimulus signal level corresponding to the point of zero crossover is obtained. The zero crossover is defined as the point of interaction of the later growth function with the zero line. This may further include determining the stimulus threshold value difference between the later stimulus threshold value and the stimulus signal threshold value.

In a further embodiment, the method includes eliciting an alert, telling an operator, such as a clinician, a threshold level corresponding to the at least one electrode is unchanged if said slope difference is equal to or below a predetermined slope difference threshold value (SDTV). This may further indicate a stimulus signal threshold value difference (SSTV) between the threshold obtained from later session and threshold received from the prior session is equal to or below a predefined stimulus signal threshold value difference. Additionally or alternatively, the method includes eliciting an alert, telling an operator, such as a clinician, that a closer examination by the operator or clinician is needed if said slope difference is above a predetermined slope difference threshold value (SDTV). This may indicate the stimulus signal threshold value difference (SSTV) between the threshold obtained from the later session and the threshold received from the prior session is above a predefined stimulus signal threshold value difference. The predetermined slope difference threshold value may include an acceptable range of variation between the prior slope and the later slope and the predefined stimulus signal threshold value difference may include an acceptable range defining a difference between the threshold value received from the prior session and that of that obtained from the later session.

According to another embodiment, there is provided a system for acquisition of evoked compound action potential (ECAP) recordings in patients, the system comprising an ECAP measurement tool and devices or modules configured to carry out the disclosed method.

In an embodiment, the devices or modules comprises storage means for storing ECAP measurements carried out at one or more previous sessions such as the prior session.

In another embodiment, the devices or modules comprises a regression line generator configured to generate a regression line from a current recording of ECAP and a comparator that is configured to compare specific measuring results from a current recording with corresponding recordings from a previous session.

In yet another embodiment, the devices and modules comprise a slope estimator adapted to determine the prior slope and the later slope and a comparator that is configured to compare the prior slope with the later slope.

In yet another embodiment, the devices and modules further include a notification generator for eliciting notifications as included in this disclosure.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
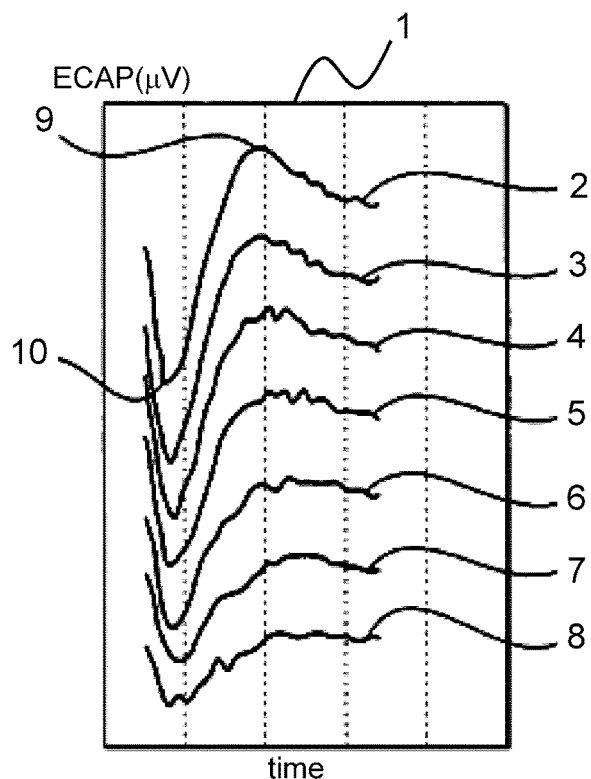
FIG. 1 shows an exemplary series of ECAP measurements showing an increasingly distinct peak and dip in the neural response as stimulus current level is increased.

The detailed description set forth below in connection with the appended drawings is intended as a description of non-limiting example embodiments of the method and system according to the present disclosure.

As an illustration, the cochlear implant is defined to typically include i) an external part including an input transducer for receiving an incoming acoustic signal from a user's surroundings and providing a corresponding electric input signal, a signal processing circuit for processing the electric input signal and for determining sequences of pulses for stimulation of the electrodes in dependence on the processed incoming acoustic signal, ii) a (typically wireless, e.g. inductive) communication link for simultaneously transmitting information about the stimulation sequences and for transferring energy to iii) an implanted part allowing the stimulation to be generated and applied to an array of electrodes, which are implantable in different locations of the cochlea allowing a stimulation of one or more hearing nerves in different frequencies of the audible range. Such systems are e.g. described in U.S. Pat. No. 4,207,441 and in U.S. Pat. No. 4,532,930. It would be apparent that the disclosure is applicable to other partially or completely implanted cochlear implant system having the array of electrodes implanted within the cochlea.

In an embodiment, the implanted portion of the cochlear implant comprises a multi-electrode array e.g. in the form of a carrier comprising a multitude of electrodes adapted for being located in the cochlea in proximity of an auditory nerve of the user. The carrier is preferably made of a flexible material to allow proper positioning of the electrodes in the cochlea such that the electrodes may be inserted in the cochlea of a recipient. Preferably, the individual electrodes are spatially distributed along the length of the carrier to provide a corresponding spatial distribution along the cochlear nerve in the cochlea when the carrier is inserted in the cochlea.

As described in previously, following the surgical implantation of a cochlear implant, the implant is typically fitted or customized to conform to the specific recipient demands. This involves the collection and determination of patient-specific parameters such as threshold levels (T levels) and maximum comfort levels (C levels) for each stimulation channel, i.e. for each of the respective electrodes in the implanted portion of the cochlear implant. The procedure is performed manually by applying stimulation pulses for each channel and receiving an indication from the implant recipient as to the level and comfort of the resulting stimulation.

According to an embodiment of the present disclosure, instead of searching for threshold responses corresponding to the individual electrodes of the implanted electrode array, which require a great amount of time, use is made of previously recorded growth function data. In a first step, stimulation is applied at a previously determined suprathreshold value. Either a stimulation current level corresponding to the threshold value determined in a prior ECAP recording for a specific frequency channel and stored in the system, or a stimulation current of a higher level could be used. The neural response corresponding to this applied stimulus current is measured (and possibly recorded in a memory in the system for subsequent use or subsequent statistical analysis purposes). In a second step it is determined if the current neural response is of the same magnitude as the previous response within a predefined degree of certainty, defined by prior neural recordings in the same configuration. Following this embodiment of a method according to the present disclosure, it is no longer needed to recollect all of the growth functions corresponding to the different electrodes (channels) of the configuration to ascertain whether or not there has been a significant change in the patient's neural response patterns.

The method according to this embodiment of the disclosure is illustrated by the following, non-limiting, example:

In a prior session an ECAP recording was carried out on electrode number 10 of the implanted electrode array and a stimulus pulse of 10 nC per phase elicited a 100 μV peak to peak neural response (+/−). If at a session today (later session), the same stimulus on the same electrode elicits a 100 μV response, then it is concluded that the functioning of the patient has not changed since the last session and a measurement was then carried out on the next electrode. However, if for example the current neural response was only 50 μV peak to peak, then this would be registered and indicated by at the measuring system and the finding would probably warrant further diagnostics i.e., repeating with the same exact parameters as in the prior recording session. Such recording parameters may include the same channel, recording delay, recording electrode, amplifier gain, number of averages, stimulation rate, artifact removal scheme, etc.

According to an embodiment of the present disclosure, the method comprises defining a threshold for the change of neural response between two (i.e. at first session and at a given subsequent session). Should a change be detected above this defined threshold, the method according to this embodiment would carry out a neural response measurement at the same electrode of the implanted array at an additional level using the same measurement method and compare the neural growth function slopes obtained at a previous session for this electrode and the actual neural growth function slope that has just been determined in the current session. If there is a "significant" change, then notification generator of the system running the method of the present disclosure can notify the clinician and the clinician can then run other tests to understand the significance of the change. For example, if the neural responses are decreasing over time it may mean that levels are set too high for the program and the patient is exhibiting deleterious neural adaptation.

Figure 2:
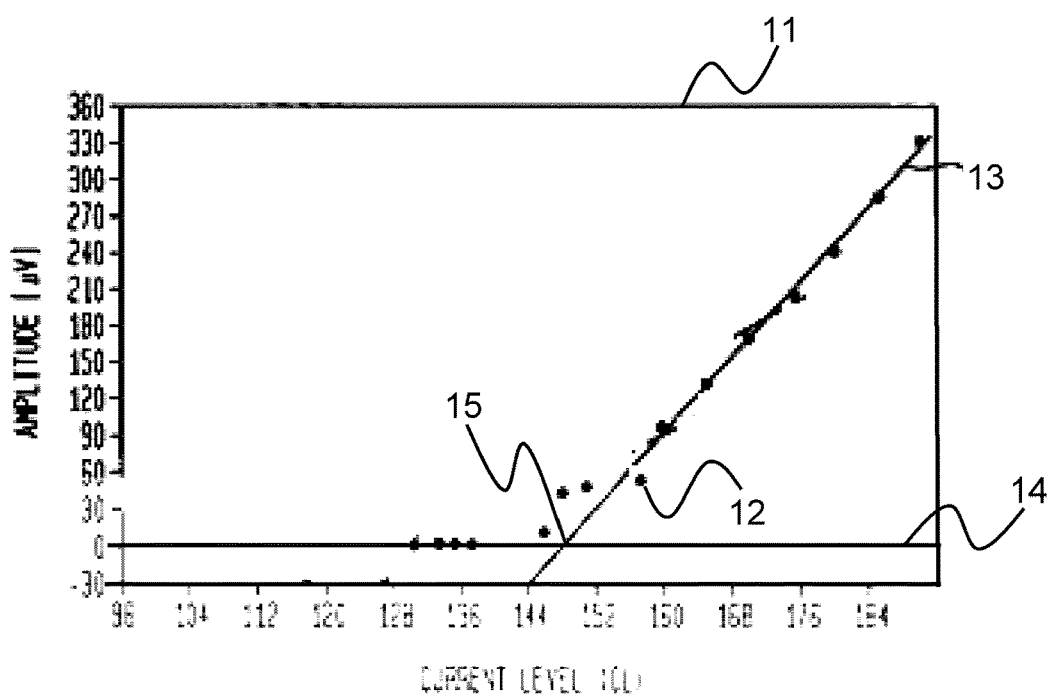
FIG. 2 shows an exemplary result of typical measurements of peak-to-peak amplitude of neural response as a function of stimulus current level.

In an embodiment, in a previously recorded growth function from the prior session, there will in most cases be a substantially linear region of growth in the middle of the I/O curve as it clearly appears in the example shown in FIG. 2. According to an embodiment of the present disclosure, the performance of a neural response measurement at an additional level the previously obtained and stored growth function would be considered for the choice of the new neural stimulus, and the system would stimulate at a lower and/or higher level to check if the SLOPE and extrapolated x intercept of the linear portion of the I/O can be considered to be stable.

Figure 3:
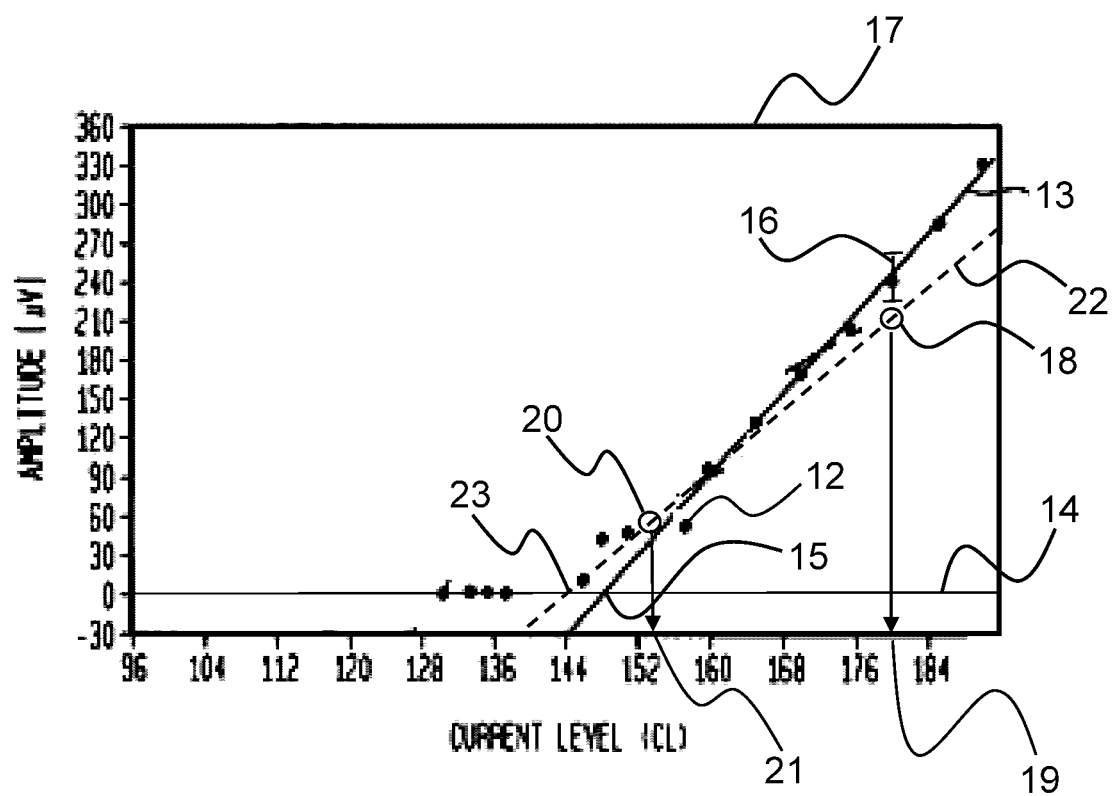
FIG. 3 illustrates an embodiment of the disclosure by means of a plot of evoked compound action potential as a function of stimulus current level obtained at a previous and a current session.

Referring now to FIG. 3, there is shown a plot 17 of evoked compound action potential as a function of stimulus current level for a specific electrode in the cochlear implant of a specific patient obtained at a previous and a current session that illustrates an embodiment of the disclosure. In a previous (prior) session the measurement results indicated by the filled dots such as 12 were obtained and the corresponding linear regression line 13 with the stimulus current threshold value determined by the intercept 15 with the zero line 14 of the evoked compound action potential was obtained. At the previous session either the actual measurement points 12 or/and these points and the regression line (i.e. the slope and zero-intercept point 15 or the equation of the regression line 13) was stored for later use.

At a current (later) session with the same patient as in the previous session—in which the same measurement set-up is used as in the previous session—a first measurement of evoked compound action potential is performed at stimulus current level 19 above the threshold value 15 found at the preceding session. If this results in an evoked compound action potential 18 outside a predefined range 16 another measurement of evoked compound action potential at same electrode is taken. In the shown example, this measurement is carried out with a stimulus current level 21, which is also above the threshold 15 determined at the previous session. The resulting evoked compound action potential is indicated at 20. Based on these two measurements 18 and 20 the line 22 through these measurement points is determined and defined by its slope S2 and interception point 23 with the zero-line 14 of the evoked compound action potential.

The regression line 13 based on the measurements performed at the previous session is thus characterized by its slope S1 and its zero line interception T1 (15) and the line 22 based on the two measurements performed at the subsequent session is characterised by its slope S2 and its zero line interception T2 (23).

In an embodiment of the disclosure, an acceptance region is defined for S1 and T1 and if S2 and T2, respectively, fall within these respective acceptance regions, the performance of the corresponding electrode in the electrode array of the cochlear implant is judged to be stable between the previous and current session and no further actions by the operator of the measurement system is needed. Similar measurements may then performed at each of the other electrode in the implant and compared with respective corresponding results obtained at the previous session.

Figure 4A:
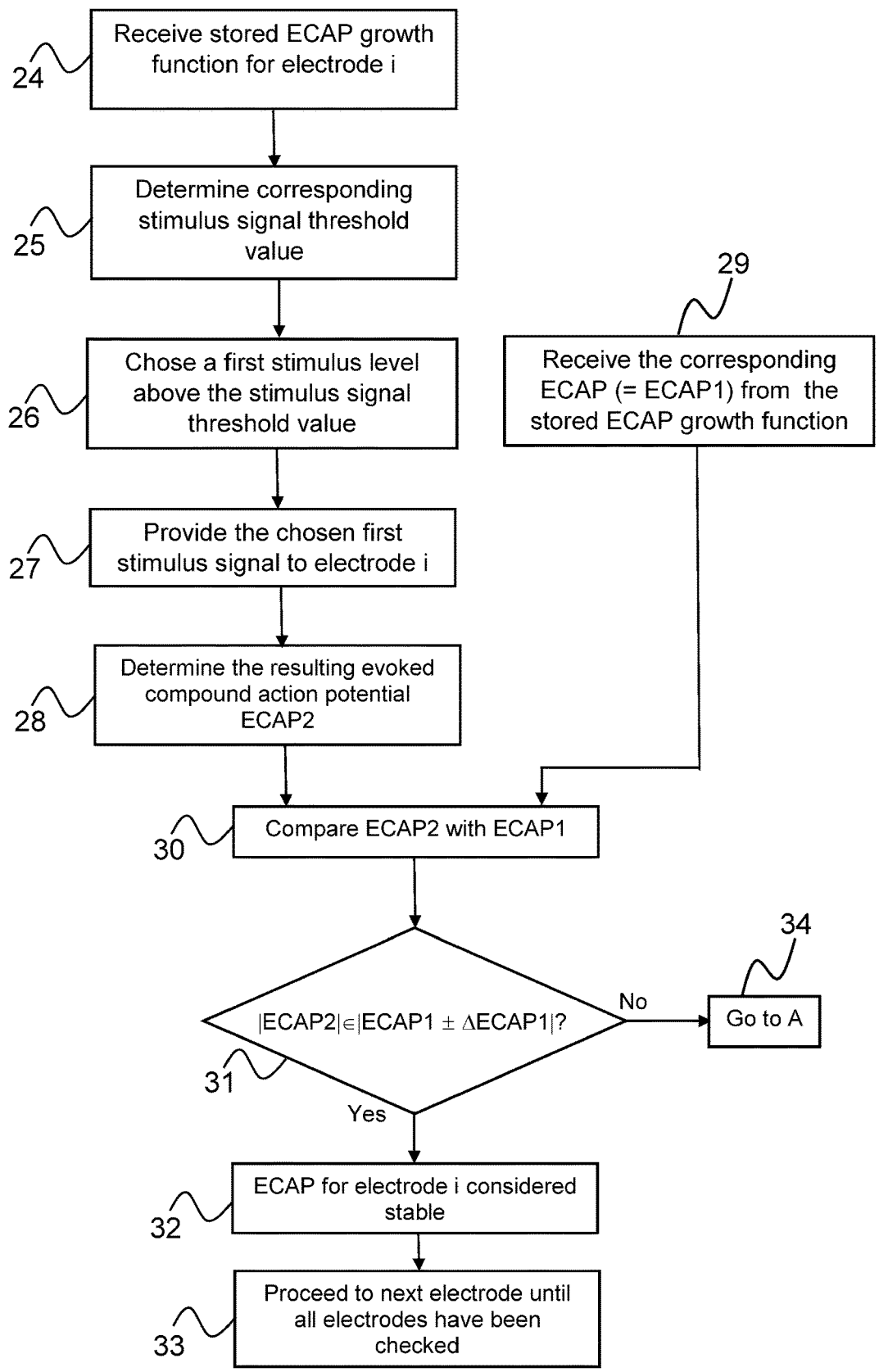
FIG. 4A shows a flow chart of the method according to an embodiment of the disclosure.
Figure 4B:
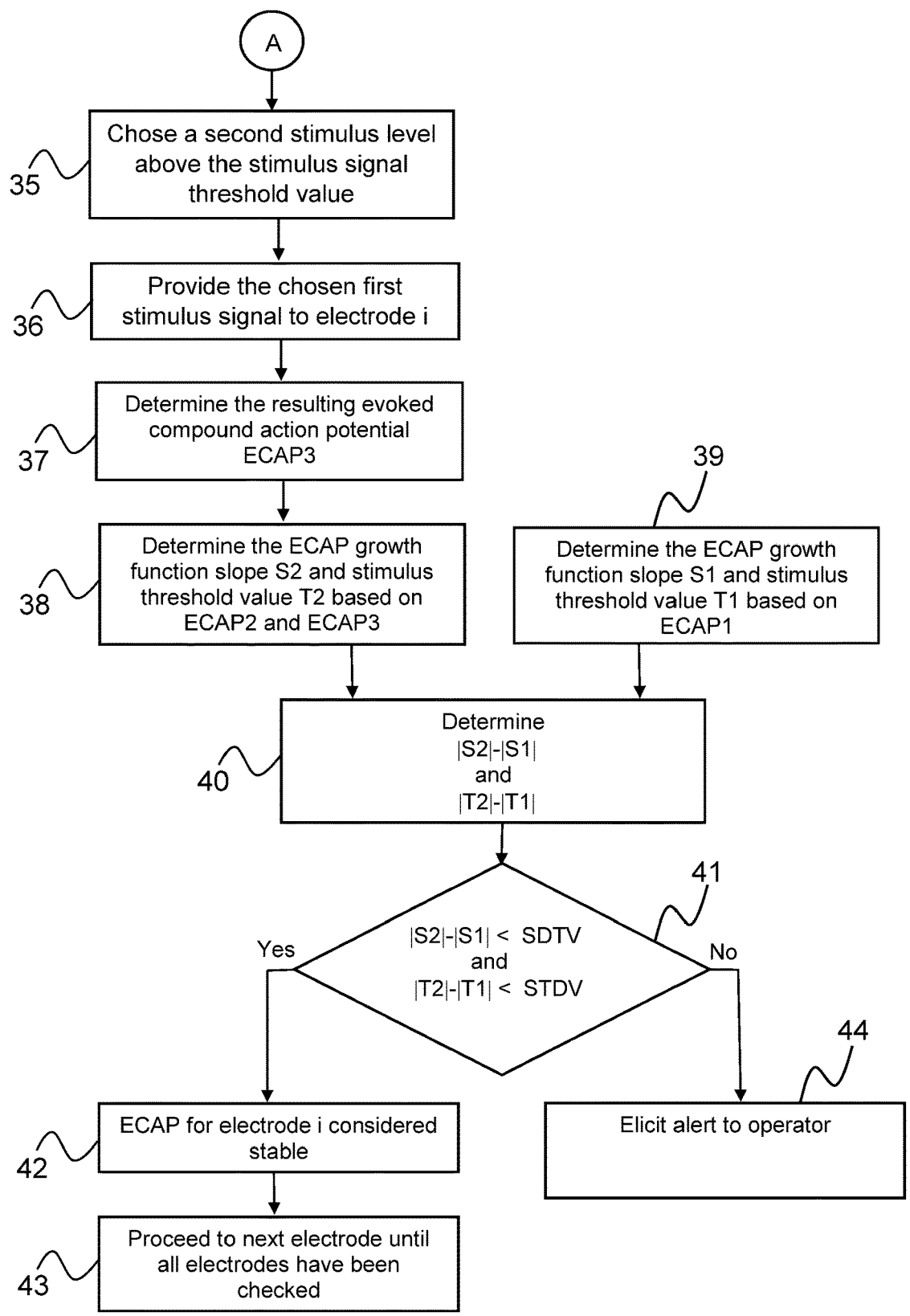
FIG. 4B shows a flow chart of an embodiment of the method according to an embodiment of the disclosure.

Referring to FIGS. 4A and 4B there is shown a flow chart of an embodiment of the method according to the disclosure.

In step 24 a stored ECAP growth function for a specific electrode (i) in a cochlear implant of a specific patient is received. The ECAP growth function has been stored at a previous session with the patient. In step 25 the corresponding stimulus signal threshold value (see for instance FIG. 2 or 3) is determined. In step 26 a first supra-threshold stimulus level is chosen and in step 29 the corresponding ECAP value from the stored ECAP growth function I provided. This value is designated by ECAP1 in FIG. 4a.

In step 27 the chosen supra-threshold stimulus level (the "first" stimulus signal level) is provided to the specific electrode (i) and in step 28 the resulting ECAP value (ECAP2) is determined.

In step 30 and 31 ECAP2 is compared with ECAP1 and if ECAP2 falls outside a predefined acceptance range ΔECAP1 the method according to this embodiment proceeds to A in the flow chart shown in FIG. 4B.

If ECAP2 is within the predefined acceptance range ΔECAP1, the ECAP for electrode i is considered stable (step 32) and the method proceeds to the next electrode as indicated in step 33.

Referring to FIG. 4B, if ECAP2 falls outside a predefined acceptance range ☐ECAP1 a second supra-threshold stimulus signal level is chosen in step 35 and this stimulus signal is provided to electrode i in step 36. In step 37 the resulting ECAP (ECAP3) is determined.

In step 38 the slope S2 of the corresponding ECAP growth function and stimulus threshold value T2 is determined based on the results ECAP2 and ECAP3.

In step 39 the ECAP growth function slope S1 and stimulus threshold value T1 is determined based on the stored ECAP1 determined at a previous session.

In step 40 the difference between the slopes S2 and S1 and the difference between the stimulus threshold values T2 and T1 are determined.

In step 41 it is investigated if the difference between the slopes S2 and S1 and between the stimulus threshold values T2 and T1, respectively, are below predefined threshold values, slope difference threshold and stimulus threshold difference threshold SDTV and STDV, respectively. If both of these requirements are fulfilled the method proceeds to step 42 where the operator is notified that the electrode response is considered stable and the method proceeds to the next electrode in step 43. If the above requirements are not fulfilled, the method proceeds to step 44, where an alert message is elicited to the operator that further investigations may be required.

The method according to the present disclosure can be implemented on an system or setup, and such an automated setup could be used at later troubleshoot sessions not only by a clinician but also by non ECAP experts at later troubleshoot sessions.

In an embodiment of the present disclosure the method according to the present disclosure may be implemented using an ECAP measurement tool supplemented by devices or modules necessary for carrying out the method of the disclosure and for storing recordings of measurements carried out at previous sessions. Such devices or modules may comprise a regression line generator to generate the regression line from the subsequent recording and a comparator that is configured to compare specific measuring results from a subsequent session with corresponding measuring results from a previous session and/or slopes of the subsequent regression line with that of the regression line from the previous recording.

Figure 5:
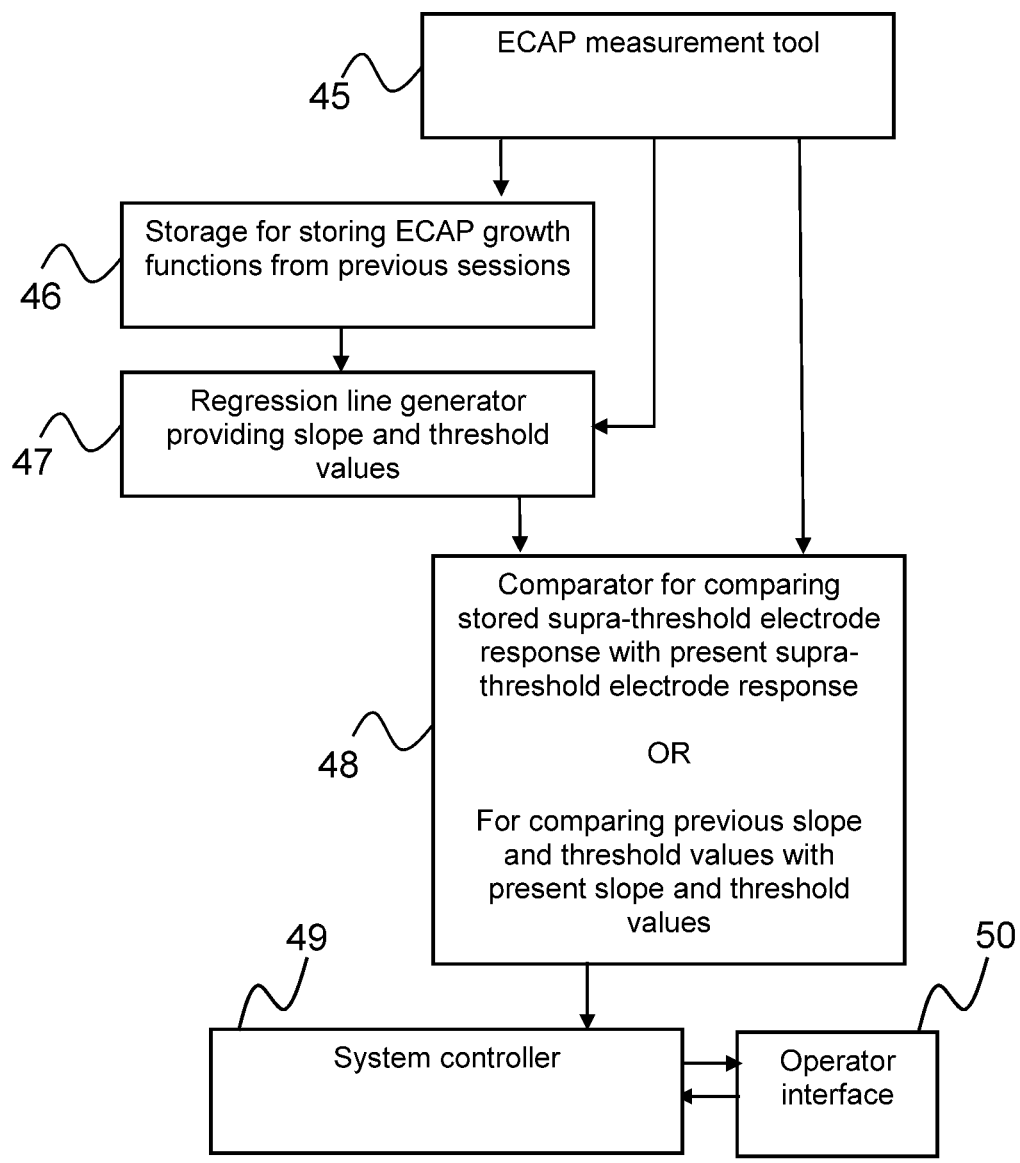
FIG. 5 shows a schematic block diagram of a system according to an embodiment of the disclosure.

Referring to FIG. 5 there is shown an embodiment of a system according to an embodiment of the disclosure. The system comprises an ECAP measurement tool 45 that is supplemented by additional functional blocks 46 through 50. It is understood that some or all of these blocks as an option may be incorporated into the ECAP measurement tool, but they can also be provided as separate external units. Specifically, they may be incorporated as software on a computer.

The system according to this embodiment comprises a storage 46 for storing ECAP growth functions (or individual ECAP measurement data) from previous sessions. In case the growth functions have not already been determined at the previous session, the regression line generator 47 may be adapted to determine the corresponding linear regression line for instance defined by its slope and point of intersection (see FIGS. 2 and 3). Thus, the regression line generator may include the functioning of the slope estimator that is adapted to determine the prior slope and the later slope The system further comprises a comparator configured to compare either stored supra-threshold electrode response with present supra-threshold electrode responses provided by means of the ECAP measurement tool 45 or to compare previous slope and threshold values with present slope and threshold values determined for instance based on the two supra-threshold measurements of ECAP as described under the first aspect. Although determining the slope and threshold values based on these two measurements does no need a regression line generator it is possible as an option to use the regression line generator 47 also for this purpose.

The various functions of the system is in the embodiment shown in FIG. 5 controlled by a separate system controller 49 which interacts with the operator interface 50. Alternatively, the ECAP measurement tool 45 may be provided with a system controller configured to control the system.

Figure 6:
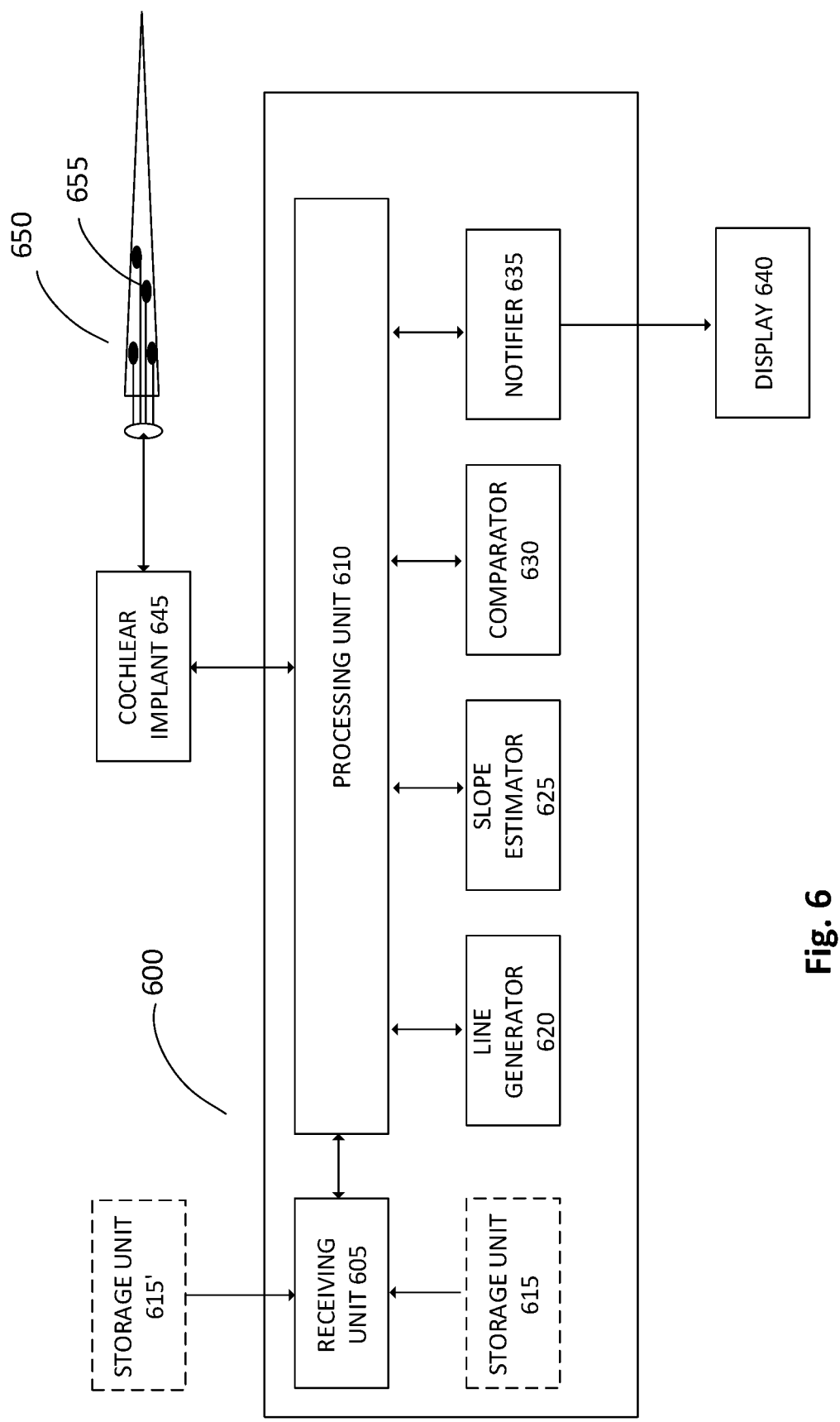
FIG. 6 illustrates a system according to an embodiment of the disclosure.

FIG. 6 illustrates a system 600 according to an embodiment of the disclosure. The system 600 is configured to acquire evoked compound action potential (ECAP) recordings at a later session for a patient provided with a cochlear implant 545 comprising an implanted array 650 of electrodes is disclosed. The system includes a receiving unit 605 and a processing unit 610. The receiving unit 605 is configured to receive, corresponding to an electrode of the implanted array of electrodes, a stored prior individual value from a plurality of stored prior individual values of evoked compound action potentials (ECAP) or an ECAP prior growth function corresponding to the stored plurality of prior individual values of the ECAP, the plurality of stored prior individual values or the ECAP prior growth function being obtained at a previous session. The processing unit 610 is configured to process the received prior individual value or ECAP growth function to determine a stimulus signal value corresponding to the received individual value or a selected point on the ECAP prior growth function, instruct a signal delivery unit to provide to the electrode a first stimulus signal comprising a first level that is same or above said stimulus signal value, and determine a resulting evoked compound action potential generated in response to said first stimulus signal.

In an embodiment, the processing unit 610 is configured to instruct a comparator 630, to determine a value difference between a value of the resulting evoked compound action potential and the received stored prior individual value from the prior session; and instruct a notifier 635, to notify that a threshold level corresponding to the electrode is unchanged if the determined value difference is equal to or below a predetermined value difference and the received stored prior individual value related to the threshold level determined in the previous session.

According to an embodiment, a regression line generator 620 is configured to generate a prior regression line based on the at least two received prior individual values and a later regression line based on the determined at least two resulting evoked compound action potentials; a slope estimator 625 is configured to determine a prior slope corresponding to the prior regression line and a later slope corresponding to the later regression line; a comparator 630 configured to compare the prior slope with the later slope and determine a slope difference between the prior slope and later slope; and the processing unit 610 is configured to instruct a notifier 635, to notify that a threshold level corresponding to the electrode is unchanged if the determined slope difference is equal to or below a predetermined slope difference value.

According to an embodiment, a regression line generator 620 is configured to generate a later regression line based on the determined at least two resulting evoked compound action potentials; a slope estimator 625 is configured to determine a prior slope of the received ECAP prior growth function and a later slope corresponding to the later regression line; a comparator 630 configured to compare the prior slope with the later slope and determine a slope difference between the prior slope and later slope; and the processing unit 610 configured to instruct a notifier 635, to notify that a threshold level corresponding to the electrode is unchanged if the determined slope difference is equal to or below a predetermined slope difference value.

According to an embodiment, a storage unit (local 615 and/or remote 615') is configured to store a prior individual value/plurality of prior individual values of evoked compound action potentials (ECAP) and/or an ECAP prior growth function corresponding to the stored plurality of prior individual values of the ECAP from the previous sessions; and provide the stored prior individual value/plurality of stored prior individual values of evoked compound action potentials (ECAP) or an ECAP prior growth function corresponding to the stored plurality of prior individual values of the ECAP in response to a request from the processing unit.

According to an embodiment, the receiver unit 605 is configured to receive a prior threshold level, corresponding to the electrode, from a previous session; or the processing unit 610 is configured to determine prior threshold level from zero crossing of the prior regression line/received ECAP growth function with a zero line.

According to an embodiment, the processing unit 610 is configured to determine a zero crossing of the later regression line with a zero line, and obtaining a later threshold value represented by the stimulus signal level corresponding to the point of zero crossing; determine a threshold value difference between the later threshold value and the prior threshold level; and instruct the notifier to notify that a threshold level corresponding to the electrode is unchanged if the determined threshold value difference is equal to or below a predetermined value difference.

According to an embodiment, the processing unit 610 is configured to instruct the notifier 635 to alert an operator to manually determine the value of the ECAP for estimating threshold level
- if the determined slope difference is above the predetermined slope difference value; and/or
- if the determined value difference or determined threshold value difference is above the predetermined value difference.

In different preceding embodiments, the notifier 635 may be configured to provide notification at a display 640.

In any preceding embodiments, the predetermined value difference and/or predetermined slope difference value is stored in the storage unit 615/615' and provided to the processing unit or comparator in response to the request command from the processing unit.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A system for acquiring evoked compound action potential (ECAP) recordings at a later session for a patient provided with a cochlear implant comprising an implanted array of electrodes, the system comprising:
   a receiving unit configured to receive, corresponding to an electrode of the implanted array of electrodes, a stored prior individual value from a plurality of stored prior individual values of evoked compound action potentials (ECAP) or an ECAP prior growth function corresponding to the stored plurality of prior individual values of the ECAP, the plurality of stored prior individual values or the ECAP prior growth function being obtained at a previous session; and
   a processing unit configured to
      process the received prior individual value or ECAP growth function to determine a stimulus signal value corresponding to the received individual value or a selected point on the ECAP prior growth function,
      instruct a signal delivery unit, the signal delivery unit being configured to provide a stimulus signal to the electrode, to provide a first stimulus signal comprising a first level that is same or above said stimulus signal value, and
      determine a resulting evoked compound action potential generated in response to said first stimulus signal.

2. The system according to claim 1, wherein processing unit is further configured to
   instruct a comparator to determine a value difference between a value of the resulting evoked compound action potential and the received stored prior individual value from the prior session; and
   instruct a notifier, the notifier configured to provide notifications, to notify that a threshold level corresponding to the electrode is unchanged when the determined value difference is equal to or below a predetermined value difference and the received stored prior individual value related to the threshold level determined in the previous session.

3. The system according to claim 2, wherein the processing unit is configured to
   determine a zero crossing of a later regression line with a zero line, and obtain a later threshold value represented by a stimulus signal level corresponding to the point of zero crossing;
   determine a threshold value difference between the later threshold value and a prior threshold level; and
   instruct the notifier to notify that a threshold level corresponding to the electrode is unchanged when the determined threshold value difference is equal to or below a predetermined value difference.

4. The system according to claim 1, wherein the system is configured to utilize same ECAP recording parameters during the later session as utilized during the previous session, the recording parameters comprising one or more of recording delay, amplifier gain, number of averages, stimulation rate, artifact removal scheme, and recording electrode.

5. The system according to claim 1, wherein
   the receiving unit is configured to receive, corresponding to the electrode of the implanted array of electrodes, at least two prior individual values from the plurality of stored prior individual values of evoked compound action potentials (ECAP) or the ECAP prior growth function corresponding to the stored plurality of prior individual values of the ECAP, the plurality of stored prior individual values or the ECAP prior growth function being obtained at the previous session; and
   the processing unit is configured to
      process the at least two received prior individual values or the ECAP prior growth function to determine at least two stimulus signal values corresponding to the at least two received prior individual values or at least two selected points on the ECAP prior growth function,
      instruct the signal delivery unit to provide to the electrode a first stimulus signal and a second stimulus signal, the first signal comprising a first level that is same or above one of the at least two stimulus signal values and the second signal comprising a second level that is same or above the other of the at least two stimulus signal values, and determine at least two resulting evoked compound action potentials elicited in response to said first stimulus signal and second stimulus signal.

6. The system according to claim 5, further comprising
a regression line generator configured to generate a prior regression line based on the at least two received prior individual values and a later regression line based on the determined at least two resulting evoked compound action potentials;
a slope estimator configured to determine a prior slope corresponding to the prior regression line and a later slope corresponding to the later regression line; and
a comparator configured to compare the prior slope with the later slope and determine a slope difference between the prior slope and later slope, wherein
the processing unit is configured to instruct the notifier to notify that a threshold level corresponding to the electrode is unchanged when the determined slope difference is equal to or below a predetermined slope difference value.

7. The system according to claim 5, further comprising
a regression line generator configured to generate a later regression line based on the determined at least two resulting evoked compound action potentials;
a slope estimator configured to determine a prior slope of the received ECAP prior growth function and a later slope corresponding to the later regression line; and
a comparator configured to compare the prior slope with the later slope and determine a slope difference between the prior slope and later slope, wherein
the processing unit is configured to instruct the notifier to notify that a threshold level corresponding to the electrode is unchanged when the determined slope difference is equal to or below a predetermined slope difference value.

8. The system according to claim 5, wherein the processing unit is configured to instruct the notifier to alert an operator to manually determine the value of the ECAP for estimating threshold level
when the determined slope difference is above the predetermined slope difference value; and/or
when the determined value difference or determined threshold value difference is above the predetermined value difference.

9. The system according to claim 8, wherein the predetermined slope difference and/or predetermined threshold value difference is based on a sample population, wherein the predetermined slope difference and/or predetermined threshold value difference is determined based on successful ECAP measurements performed manually during multiple subsequent sessions for each CI user included in a sample population.

10. The system according to claim 1, further comprising a storage unit configured to
store a prior individual value/plurality of prior individual values of evoked compound action potentials (ECAP), and/or an ECAP prior growth function corresponding to the stored plurality of prior individual values of the ECAP from the previous sessions; and
provide the stored prior individual value/plurality of stored prior individual values of evoked compound action potentials (ECAP) or an ECAP prior growth function corresponding to the stored plurality of prior individual values of the ECAP in response to a request from the processing unit.

11. The system according to claim 1, wherein
the receiver unit is configured to receive a prior threshold level, corresponding to the electrode, from a previous session; or
the processing unit is configured to determine a prior threshold level from zero crossing of a prior regression line or a received ECAP growth function with a zero line.

12. A non-transitory computer readable medium encoded with instructions, which when executed by a system, causes the system to
receive, corresponding to an electrode of the implanted array of electrodes, a stored prior individual value from a plurality of stored prior individual values of evoked compound action potentials (ECAP) or an ECAP prior growth function corresponding to the stored plurality of prior individual values of the ECAP, the plurality of stored prior individual values or the ECAP prior growth function being obtained at a previous session;
process the received prior individual value or ECAP growth function to determine a stimulus signal value corresponding to the received individual value or a selected point on the ECAP prior growth function,
instruct a signal delivery unit, the signal delivery unit being configured to provide a stimulus signal to the electrode, to provide a first stimulus signal comprising a first level that is same or above said stimulus signal value,
determine a resulting evoked compound action potential generated in response to said first stimulus signal.

13. The non-transitory computer readable medium according to claim 12, wherein when executed by the system, the encoded instructions further cause the system to
instruct a comparator to determine a value difference between a value of the resulting evoked compound action potential and the received stored prior individual value from the prior session; and
instruct a notifier, the notifier configured to provide notifications, to notify that a threshold level corresponding to the electrode is unchanged when the determined value difference is equal to or below a predetermined value difference and the received stored prior individual value related to the threshold level determined in the previous session.

14. The non-transitory computer readable medium according to claim 13, wherein when executed by the system, the encoded instructions further cause the system to
determine a zero crossing of a later regression line with a zero line, and obtain a later threshold value represented by a stimulus signal level corresponding to the point of zero crossing;
determine a threshold value difference between the later threshold value and a prior threshold level; and
instruct the notifier to notify that a threshold level corresponding to the electrode is unchanged when the determined threshold value difference is equal to or below a predetermined value difference.

15. The non-transitory computer readable medium according to claim 12, wherein when executed by the system, the encoded instructions further cause the system to
generate, using a regression line generator, a prior regression line based on the at least two received prior individual values and a later regression line based on the determined at least two resulting evoked compound action potentials;
determine, using a slope estimator, a prior slope corresponding to the prior regression line and a later slope corresponding to the later regression line;

compare, using a comparator, the prior slope with the later slope and determine a slope difference between the prior slope and later slope; and instruct a notifier configured to provide notifications, to notify that a threshold level corresponding to the electrode is unchanged when the determined slope difference is equal to or below a predetermined slope difference value.

16. The non-transitory computer readable medium according to claim 12, wherein when executed by the system, the encoded instructions further cause the system to generate, using a regression line generator, a later regression line based on the determined at least two resulting evoked compound action potentials;

determine, using a slope estimator, a prior slope of the received ECAP prior growth function and a later slope corresponding to the later regression line;

compare, using a comparator, the prior slope with the later slope and determine a slope difference between the prior slope and later slope; and instruct a notifier configured to provide notifications, to notify that a threshold level corresponding to the electrode is unchanged when the determined slope difference is equal to or below a predetermined slope difference value.

17. A method for acquiring evoked compound action potential (ECAP) recordings at a later session for a patient provided with a cochlear implant comprising an implanted array of electrodes, the method comprising:

receiving, corresponding to an electrode of the implanted array of electrodes, a stored prior individual value from a plurality of stored prior individual values of evoked compound action potentials (ECAP) or an ECAP prior growth function corresponding to the stored plurality of prior individual values of the ECAP, the plurality of stored prior individual values or the ECAP prior growth function being obtained at a previous session;

processing the received prior individual value or ECAP growth function to determine a stimulus signal value corresponding to the received individual value or a selected point on the ECAP prior growth function;

instructing a current delivery unit, the current signal delivery unit being configured to provide a stimulus signal to the electrode, to provide a first stimulus current signal comprising a first level that is same or above said stimulus signal value; and determining a resulting evoked compound action potential elicited in response to said first stimulus signal.

18. The method according to claim 17, further comprising determining a value difference between a value of the resulting evoked compound action potential and the received stored prior individual value from the prior session; and notifying that a threshold level corresponding to the electrode is unchanged when the determined value difference is equal to or below a predetermined value difference and the received stored prior individual value related to the threshold level determined in the previous session.

19. The method according to claim 17, further comprising generating a later regression line based on the determined at least two resulting evoked compound action potentials with or without generating a prior regression line based on the at least two received prior individual values;

determining a prior slope corresponding to the prior regression line/ECAP prior growth function and a later slope corresponding to the later regression line;

comparing the prior slope with the later slope and determining a slope difference between the prior slope and later slope; and notifying a threshold level corresponding to the electrode is unchanged when the determined slope difference is equal to or below a predetermined slope difference value.

20. The method according to claim 17, further comprising determining a zero crossing of a later regression line with a zero line, and obtaining a later threshold value represented by a stimulus signal level corresponding to the point of zero crossing;

determining a threshold value difference between the later threshold value and the prior threshold level; and notifying that a threshold level corresponding to the electrode is unchanged when the determined threshold value difference is equal to or below a predetermined value difference.

* * * * *